(12) United States Patent
Waters et al.

(10) Patent No.: US 8,518,641 B2
(45) Date of Patent: Aug. 27, 2013

(54) DNA DAMAGE TESTING

(75) Inventors: Raymond Waters, Swansea (GB); Simon Huw Reed, Glamorgan (GB)

(73) Assignee: University College Cardiff Consultants Limited, Cardiff (GB)

( * ) Notice: Subject to any disclaimer, the term of this patent is extended or adjusted under 35 U.S.C. 154(b) by 602 days.

(21) Appl. No.: 12/666,493

(22) PCT Filed: Jun. 27, 2008

(86) PCT No.: PCT/GB2008/002248
§ 371 (c)(1),
(2), (4) Date: Dec. 23, 2009

(87) PCT Pub. No.: WO2009/001111
PCT Pub. Date: Dec. 31, 2008

(65) Prior Publication Data
US 2010/0179070 A1    Jul. 15, 2010

(30) Foreign Application Priority Data
Jun. 28, 2007    (GB) .................................. 0712584.2

(51) Int. Cl.
*C12Q 1/68*    (2006.01)
*C12N 9/00*    (2006.01)
*C07K 16/00*    (2006.01)

(52) U.S. Cl.
USPC .......................... 435/6.1; 435/183; 530/387.1

(58) Field of Classification Search
None
See application file for complete search history.

(56) References Cited

U.S. PATENT DOCUMENTS

| 5,629,314 | A | 5/1997 | Gaskin | |
|---|---|---|---|---|
| 2004/0014083 | A1* | 1/2004 | Yuan et al. | 435/6 |
| 2005/0255502 | A1* | 11/2005 | D'Andrea | 435/6 |

FOREIGN PATENT DOCUMENTS

| CA | 1 258 624 | 8/1989 |
|---|---|---|
| WO | WO 01/62968 | 8/2001 |

OTHER PUBLICATIONS

Meier, et al.; "Spreading of mammalian DNA-damage response factors studied by ChIP-chip at damaged telomeres"; European Molecular Biology Organization; The EMBO Journal (2007), vol. 26, No. 11, pp. 2707-2718.
Altaf A. Wani and Jasna Arezina "Immunoanalysis of ultraviolet radiation induced DNA damage and repair within specific gene segments of plasmid DNA", 1991 Biochimica et Biophysica Acta (BBA)—Gene Structure and Expression vol. 1090, Issue 2, Oct. 8, 1991, pp. 195-203 Copyright © 1991 Published by Elsevier Science B.V. Received Jan. 30, 1991 Department of Radiology and Biochemistry Program, The Ohio State University, Columbus, OH, U.S.A.

* cited by examiner

*Primary Examiner* — Kenneth R. Horlick
*Assistant Examiner* — David Thomas
(74) *Attorney, Agent, or Firm* — King & Schickli, PLLC

(57) ABSTRACT

The invention relates to a method of for detecting DNA damage in a tissue sample. The method includes the steps of exposing sample DNA to a tagged DNA-damage binding factor and then shearing the DNA to produce fragments. After separating damaged from undamaged DNA, the two are amplified and differentially labeled. The labeled fragments can be immobilized on a microarray allowing the location and extent of any DNA damage to be determined.

54 Claims, 2 Drawing Sheets

DNA DAMAGE TESTING

TECHNICAL FIELD

The invention relates to a method for detecting DNA damage in a sample; a diagnostic kit for undertaking the said method, including components thereof; and a screening method for screening compounds to identify either whether they damage DNA or whether damaged DNA is affected thereby.

BACKGROUND OF THE INVENTION

Maintenance of the structure of the eukaryotic genome involves a series of proteins such as, but not exclusively, enzymes which not only monitor DNA for alterations but also effect repairs to any alterations with a view to maintaining the integrity of the DNA for the purpose of subsequent meiosis or mitosis.

Different agents cause different types of DNA damage and, as a result, a different series of proteins have evolved in order to repair the different types of damage.

It follows that DNA repair is one of the fundamental processes involved in DNA metabolism and defects in any of the DNA repair mechanisms have major biological consequences, including a significant impact on the well-being of the relevant organism.

A main goal since the discovery of the structure of DNA has been to systematically determine the precise molecular mechanisms that mediate DNA function.

As improved technologies allow for increasingly high resolution studies of DNA it is becomingly increasingly possible to undertake location analysis of DNA, i.e. analysis that enables the precise location of a given event to be determined within the eukaryotic genome. When one considers that the human cell contains 2 metres of DNA packed within chromatin and that these 2 metres of DNA comprise more than 30,000 genes or 3.2 billion base pairs but one is, nevertheless, able to pinpoint the precise location of a given event (within a 100 base pair degree of accuracy) then one begins to appreciate that location analysis is an important tool in understanding events that take place within the genome.

There are a number of agents within the environment which are thought to damage DNA. These agents are both chemical and physical and so comprise genotoxic molecules, typically, man-made, and also physical forces such as electromagnetic radiation such as UV rays and X-rays.

UV rays are known to be particularly damaging to humans and are the commonest cause of skin cancer due to epidermal absorption of ultraviolet radiation. For cancer DNA is believed to be the primary target and it has been shown that photochemical reactions involving DNA have been linked to mutagenesis, carcinogenesis and cell death. Damage caused by UV exposure is characterised by the formation of pyrimidine dimers and in particular thymine dimers. Nature has responded by producing an enzyme, photolyase, which reactivates DNA by the direct repair of thymine dimers. It binds to the damaged DNA and by absorbing energy restores the pyrimidine dimers to their former monomeric state. This repair mechanism is found in many forms of eukaryotic life.

In an analogous fashion other DNA repair proteins, and in particular enzymes, have evolved to repair other forms of DNA damage. Examples of such enzymes include base excision repair enzymes; enzymes which are responsible for direct reversal of damage, repair of DNA-protein crosslinks, mismatch excision repair, nucleotide excision repair, homologous recombination, non-homologous end joining or modulation of nucleotide pools; DNA polymerases, editing and processing nucleases, also gene products which interfere with the Rad6 pathway or which affect chromatin structure, enzymes or gene products encoded by genes which are defective in diseases associated with sensitivity to DNA damaging agents etc. Table 1 lists examples of genes encoding these enzymes and other proteins 1 along with an indication of their functionality and so the nature of the damage that they repair. Many of these enzymes are highly conserved and so homologues exist in different species.

TABLE 1

Genes Encoding DNA Repair Enzymes or having a DNA Repair function

| Gene Name (Synonyms) | Activity | Chromosome Location | NCBI Accession No. |
|---|---|---|---|
| Base excision repair | DNA glycosylases: major altered base released | | |
| UNG | U | 12q24.11 | NM 080911 |
| SMUG1 | U | 12q13.13 | NM 014311 |
| MBD4 | U or T opposite G at CpG sequences | 3q21.3 | NM 003925 |
| TDG | U, T or ethenoC opposite G | 12q23.3 | NM 003211 |
| OGG1 | 8-oxoG opposite C | 3p25.3 | NM 016821 |
| MUTYH (MYH) | A opposite 8-oxoG | 1p34.1 | NM 012222 |
| NTHL1 (NTH1) | Ring-saturated or fragmented pyrimidines | 16p13.3 | NM 002528 |
| MPG | 3-MeA, ethenoA, hypoxanthine | 16p13.3 | NM 002434 |
| NEIL1 | Removes thymine glycol | 15q24.2 | NM 024608 |
| NEIL2 | Romoves oxidative products of pyrimidines Other BER Factors | 8p23.1 | NM 145043 |
| APEX1 | AP endonuclease | 14q11.2 | NM 001641 |
| APEX2 | AP endonuclease | Xp11.21 | NM 014481 |
| LIG3 | DNA Ligase | 17q12 | NM 013975 |
| XRCC1 | Ligase accessory factor | 19q13.31 | NM 006297 |
| PNKP | Converts some DNA breaks to ligatable ends | 19q13.33 | NM 007254 |

TABLE 1-continued

Genes Encoding DNA Repair Enzymes or having a DNA Repair function

| Gene Name (Synonyms) | Activity | Chromosome Location | NCBI Accession No. |
|---|---|---|---|
| | Poly (ADP-ribose) polymerase (PARP) enzymes | | |
| PARP1 (ADPRT) | Protects strand interruptions | 1q42.12 | NM 001618 |
| PARP2 (ADPRTL2) | PARP-like enzyme | 14q11.2 | NM 005484 |
| Direct Reversal of Damage | | | |
| MGMT | $O^6$-meG alkyltransferase | 10q26.3 | NM 002412 |
| MGC90512 (ABH2) | 1-meA dioxygenase | 12q24.11 | NM 001655 |
| DEPC-1 (ABH3) | 1-meA dioxygenase | 11p11.2 | NM 139178 |
| Repair of DNA-protein cross links | | | |
| TDP1 | Removes covalently bound TOP1-DNA complexes | 14q32.11 | NM 018319 |
| Mismatch excision repair (MMR) | | | |
| MSH2 | Mismatch and loop recognition | 2p21 | NM 000251 |
| MSH3 | Mismatch and loop recognition | 5q14.1 | NM 002439 |
| MSH6 | Mismatch and loop recognition | 2p16.3 | NM 000179 |
| MSH4 | MutS homologues specialised for meiosis | 1p31.1 | NM 002440 |
| MSH5 | MutS homologues specialised for meiosis | 6p21.33 | NM 002441 |
| PMS1 | MutL homologue | 2q32.2 | NM 000534 |
| MLH1 | MutL homologues forming heterodimer | 3p22.3 | NM 000249 |
| PMS2 | MutL homologues forming heterodimer | 7p22.1 | NM 000535 |
| MLH3 | MutL homologues of unknown function | 14q24.3 | NM 014381 |
| PMS2L3 | MutL homologues of unknown function | 7q11.23 | D38437 |
| PMS2L4 (PMS6) | MutL homologues of unknown function | 7q11.21 | D38500 |
| Nucleotide excision repair (NER) | (XP = xeroderma pigmentosum) | | |
| XPC | Binds damaged DNA as complex | 3p25.1 | NM 04628 |
| RAD23B (HR23B) | Binds damaged DNA as complex | 9q31.2 | NM 002874 |
| CETN2 | Binds damaged DNA as complex | Xq28 | NM 004344 |
| RAD23A (HR23A) | Substitutes for HR23B | 19p13.13 | NM 005053 |
| XPA | Binds damaged DNA in preincision complex | 9q22.33 | NM 000380 |
| RPA1 | Binds DNA in preincision complex | 17p13.3 | NM 002945 |
| RPA2 | Binds DNA in preincision complex | 1p35.3 | NM 002946 |
| RPA3 | Binds DNA in preincision complex | 7p21.3 | NM 002947 |
| TF11H | Catalyses unwinding in preincision complex | | |
| ERCC3 (XPB) | 3' to 5' DNA helicase | 2q14.3 | NM 000122 |
| ERCC2 (XPD) | 5' to 3' DNA helicase | 19q13.32 | NM 000400 |
| GTF2H1 | Core TFIIH subunit p62 | 11p15.1 | NM 005316 |
| GTF2H2 | Core TFIIH subunit p44 | 5q13.2 | NM 001515 |
| GTF2H3 | Core TFIIH subunit p34 | 12q24.31 | NM 001516 |
| GTF2H4 | Core TFIIH subunit p52 | 6p21.33 | NM 001517 |
| GTF2H5 (TTDA) | Core TFIIH subunit p8 | 6p25.3 | NM 207118 |
| CDK7 | Kinase subunit of TFIIH | 5q13.2 | NM 001799 |
| CCNH | Kinase subunit of TFIIH | 5q14.3 | NM 001239 |
| MNAT1 | Kinase subunit of TFIIH | 14q23.1 | NM 002431 |
| ERCC5 (XPG) | 3' incision | 13q33.1 | NM 000123 |

TABLE 1-continued

Genes Encoding DNA Repair Enzymes or having a DNA Repair function

| Gene Name (Synonyms) | Activity | Chromosome Location | NCBI Accession No. |
|---|---|---|---|
| ERCC1 | 5'incision subunit | 19q13.32 | NM 001983 |
| ERCC4 (XPF) | 5'incision subunit | 16p13.12 | NM 005236 |
| LIG1 | DNA joining | 19q13.32 | NM 000234 |
| NER-related | | | |
| CKN1 (CSA) | Cockayne syndrome; needed for transcription-coupled NER | 5q12.1 | NM 000082 |
| ERCC6 (CSB) | Cockayne syndrome; needed for transcription-coupled NER | 10q11.23 | NM 000124 |
| XAB2 (HCNP) | Cockayne syndrome; needed for transcription-coupled NER | 19p13.2 | NM 020196 |
| DDB1 | Complex defective in XP group E | 11q12.2 | NM 001923 |
| DDB2 | Complex defective in XP group E | 11p11.2 | NM 000107 |
| MMS19L (MMS19) | Transcription and NER | 10q24.1 | NM 022362 |
| Homologous Recombination | | | |
| RAD51 | Homologous pairing | 15q15.1 | NM 002875 |
| RAD51L1 (RAD51B) | Rad51 homologue | 14q24.1 | NM 002877 |
| RAD51C | Rad51 homologue | 17q23.2 | NM 002876 |
| RAD51L3 (RAD51D) | Rad51 homologue | 17q12 | NM 002878 |
| DMC1 | Rad51 homologue, meiosis | 22q13.1 | NM 007068 |
| XRCC2 | DNA break and crosslink repair | 7q36.1 | NM 005431 |
| XRCC3 | DNA break and crosslink repair | 14q32.33 | NM 005432 |
| RAD52 | Accessory factors for recombination | 12p13.33 | NM 002879 |
| RAD54L | Accessory factors for recombination | 1p34.1 | NM 003579 |
| RAD54B | Accessory factors for recombination | 8q22.1 | NM 012415 |
| BRCA1 | Accessory factor for transcription and recombination, E3 Ubiquitin ligase | 17q21.31 | NM 007295 |
| BRCA2 (FANCD1) | Cooperation with RAD51 essential function | 13q13.1 | NM 000059 |
| SHFM1 (DSS1) | BRCA2 associated | 7q21.3 | NM 006304 |
| RAD50 | ATPase in complex with MRE11A, NBS1 | 5q23.3 | NM 005732 |
| MRE11A | 3'exonuclease | 11q21 | NM 005590 |
| NBS1 | Mutated in Nijmegen breakage syndrome | 8q21.3 | NM 002485 |
| MUS81 | A structure specific DNA nuclease | 11q13.1 | NM 025128 |
| EME1 (MMS4L) | A structure specific DNA nuclease | 17q21.33 | NM 152463 |
| EME2 | Essenital meiotic endonuclease 1 homologue 2 | 16p13.3 | NM 0010865 |
| Non-homologous end-joining | | | |
| G22P1 (Ku70) | DNA end binding | 22q13.2 | NM 001469 |
| XRCC5 (Ku80) | DNA end binding | 2q35 | NM 021141 |
| PRKDC | DNA-dependent protein kinase catalytic subunit | 8q11.21 | NM 006904 |
| LIG4 | Ligase | 13q33.3 | NM 002312 |
| XRCC4 | Ligase accessory factor | 5q14.2 | NM 003401 |
| DCLRE1C (Artemis) | Nuclease | 10p13 | NM 022487 |
| XLF (Cernunnos, NHEJ1) | XRCC4-LIG4 interacting factor | 2q35 | NM 024782 |
| Modulation of nucleotide pools | | | |
| NUDT1 (MTH1) | 8-oxoGTPase | 7p22.3 | NM 002452 |
| DUT | dUTPase | 15q1.1 | NM 001948 |

TABLE 1-continued

Genes Encoding DNA Repair Enzymes or having a DNA Repair function

| Gene Name (Synonyms) | Activity | Chromosome Location | NCBI Accession No. |
|---|---|---|---|
| RRM2B (p53R2) | P53-inducible ribonucleotide reductase small subunit 2 homologue | 8q22.3 | NM 015713 |
| DNA polymerases (catalytic subunits) | | | |
| POLB | BER in nuclear DNA | 8p11.21 | NM 002690 |
| POLG | BER in mitochondrial DNA | 15q26.1 | NM 002693 |
| POLD1 | NER and MMR | 19q13.33 | NM 002691 |
| POLE | NER and MMR | 12q24.33 | NM 006231 |
| PCNA | Sliding clamp for pol delta and pol epsilon | 20p12.3 | NM 002592 |
| REV3L (POLZ) | DNA pol zeta catalytic subunit, essential function | 6q231 | NM 002912 |
| MAD2L2 (REV7) | DNA pol zeta subunit | 1p36.22 | NM 006341 |
| REV1L (REV1) | dCMP transferase | 2q11.2 | NM 016316 |
| POLH | XP variant | 6p21.1 | NM 006502 |
| POLI (RAD30B) | Lesion bypass | 18q21.2 | NM 007195 |
| POLQ | DNA crosslink repair | 3q13.33 | NM 006596 |
| POLK (DINB1) | Lesion bypass | 5q13.3 | NM 016218 |
| POLL | Gap-filling during non-homologous end joining | 10q24.32 | NM 013274 |
| POLM | Gap filing during non-homologous end joining | 7p13 | NM 013284 |
| POLN (POL4P) | DNA crosslink repair? | 4p16.3 | NM 181808 |
| Editing and Processing nucleases | | | |
| FEN1 (DNase IV) | 5' nuclease | 11q12.2 | NM 004111 |
| TREX1 (DNase III) | 3'exonuclease, 3' alternative ORF of the TREX1/ATRIP gene | 3p21.31 | NM 033629 |
| TREX2 | 3' exonuclease | Xq28 | NM 007205 |
| EXO1 (HEX1) | 5' exonuclease | 1q43 | NM 003686 |
| SPO11 | Endonuclease | 20q13.32 | NM 012444 |
| FLJ35220 (ENDOV) | Incision 3' of hypoxanthine and uracil | 17q25.3 | NM 173627 |
| Rad6 pathway | | | |
| UBE2A (RAD6A) | Ubiquitin-conjugating enzyme | Xq24-q25 | NM 003336 |
| UBE2B (RAD6B) | Ubiquitin-conjugating enzyme | 5q31.1 | NM 003337 |
| RAD18 | E3 unbiquitin ligase | 3p25.3 | NM 020165 |
| UBE2V2 (MMS2) | Ubiquitin-conjugating complex | 8q11.21 | NM 003350 |
| UBE2N (UBC13) | Ubiquitin-conjugating complex | 12q22 | NM 003348 |
| Chromatin Structure | | | |
| H2AFX (H2AX) | Histone, phosphorylated after DNA damage | 11q23.3 | NM 002105 |
| CHAF1A (CAF1) | Chromatin assembly factor | 19p13.3 | NM 005483 |
| Genes defective in diseases associated with sensitivity to DNA damaging agents | | | |
| BLM | Bloom syndrome helicase | 15q26.1 | NM 000057 |
| WRN | Werner syndrome helicase/3'exonuclease | 8p12 | NM 000553 |
| RECQL4 | Rothmund-Thompson syndrome | 8q24.3 | NM 004260 |
| ATM | Ataxia telangiectasia | 11q22.3 | NM 000051 |
| Fanconi anaemia | | | |
| FANCA | Involved in tolerance or repair of DNA crosslinks | 16q24.3 | NM 000135 |

TABLE 1-continued

Genes Encoding DNA Repair Enzymes or having a DNA Repair function

| Gene Name (Synonyms) | Activity | Chromosome Location | NCBI Accession No. |
|---|---|---|---|
| FANCB | Involved in tolerance or repair of DNA crosslinks | Xp22.31 | NM 152633 |
| FANCC | Involved in tolerance or repair of DNA crosslinks | 9q22.32 | NM 000136 |
| FANCD2 | Involved in tolerance or repair of DNA crosslinks | 3p25.3 | NM 033084 |
| FANCE | Involved in tolerance or repair of DNA crosslinks | 6p21.31 | NM 021922 |
| FANCF | Involved in tolerance or repair of DNA crosslinks | 11p14.3 | NM 022725 |
| FANCG (XRCC9) | Involved in tolerance or repair of DNA crosslinks | 9p13.3 | NM 004629 |
| FANCL | Involved in tolerance or repair of DNA crosslinks | 2p16.1 | NM 018062 |
| FANCJ (BRIP1, BACH1) | BRCA1-associated DNA helicase | 17q23.2 | NM 032043 |
| FANCM | DNA helicase and possible nuclease in the XPF-Hef-Mus81 family | 14q21.3 | XM 048128 |
| FANCN (PALB2) | PALB2 partner and localizer of BRCA2 | 16p12.1 | NM 024675 |
| FAAP24 (C19orf40) | Fanconi anaemia-associated protein, 24 kDa | 19q13.11 | NM 152266 |
| Other identified Genes with a suspected DNA repair function | | | |
| DCLRE1A (SNM1) | DNA crosslink repair | 10q253. | NM 014881 |
| DCLRE1B (SNM1B) | Related to SNM1 | 1p13.2 | NM 022836 |
| RPA4 | Similar to RPA2 | Xp21.33 | NM 103347 |
| APTX (aprataxin) | Processing of DNA single-strand interruption | 9p21.1 | NM 175073 |
| NEIL3 | Resembles NEIL1 and NEIL3 | 4q34.3 | NM 018248 |
| RECQL (RECQ1) | DNA helicase | 12p12.1 | NM 002907 |
| RECDQL5 | DNA helicase | 17q25.1 | NM 00100371 |
| HEL308 | DNA helicase | 4q21.23 | NM 133636 |
| RAD52B (RDM1) | Similar to RAD52 | 17q12 | NM 145654 |
| Other conserved DNA damage response genes | | | |
| ATR | ATM- and I-3K-like essential kinase | 3q23 | NM 001184 |
| RAD1 | PCNA-like DNA damage sensors | 5p13.2 | NM 002853 |
| RAD9A | PCNA-like DNA damage sensors | 11q13.2 | NM 004854 |
| HUS1 | PCNA-like DNA damage sensors | 7p12.3 | NM 004507 |
| RAD17 (RAD24) | RFC-like DNA damage sensor | 5q13.2 | NM 002873 |
| CHEK1 | Effector kinase | 11q24.2 | NM 001274 |
| CHEK2 | Effector kinase | 22q12.1 | NM 007194 |
| TP53 | Regulation of the cell cycle | 17p13.1 | NM 000546 |
| ATRIP (TREX1) | ATR-interacting protein 5'alternative ORF of the TREX1/ATRIP gene | 3p21.31 | NM 130384 |
| TELO2 (Hclk2, kiaa0683) | TEL2, telomere maintenance 2, homologue | 16p13.3 | NM 016111 |

SUMMARY OF THE INVENTION

Our investigations have led us to develop a method for location analysis of DNA damage which enables us to determine not only the amount of DNA damage, when DNA is subjected to a particular agent, but also the precise location of the damage and so the functional significance thereof. Our invention, in part, involves the use of microarrays, or chips, which, as the man skilled in the art will appreciate, are solid phase arrays of DNA wherein either the whole genome of a given organism or a selected part thereof, such as a selected gene or genes, is/are deposited in a segmented, but overlapping fashion, on a given substrate. In this way, the whole of the genome, or indeed a specific gene, or part thereof, is represented on the substrate but in a series of manageable, yet overlapping, segments. The hybridisation of sample DNA to the substrate enables the precise location of the sample to be determined having regard to the genome or gene that is deposited on the substrate. Given the resolution of this technology it is possible, dependent upon the species to be examined, to determine the precise location of the sample DNA within 5 (yeast) or 100 (human) base pairs.

According to a first aspect of the invention there is therefore provided a method for detecting DNA damage in a tissue sample comprising:
1. obtaining a sample of DNA from the tissue sample;
2. exposing said DNA to at least one selected DNA damage binding factor, which factor has been tagged with a given binding molecule;
3. shearing the DNA to produce fragments thereof;
4. precipitating those fragments that include, or are associated with the tagged repair protein by binding the said tag to a selected binding partner in order to isolate fragments of DNA that include, or are associated with, said DNA repair protein; optionally
5. amplifying and labelling the precipitated fragments; and
6. exposing said optionally amplified and labelled precipitated fragments to a selected microarray under conditions that enable the fragments to hybridise to the array whereby the location of any, or the, DNA damage can be determined having regard to the location of the hybridisation fragments with respect to the array;

wherein step (2) may be carried out either before or after step (3).

The microarray will be chosen according to the species being examined. Thus, if DNA damage is being detected in yeast, then the array may be a genome wide yeast array whereas if DNA damage in humans is being detected, the array may comprise an array covering the entire human genome or a relevant part of the genome.

The DNA-damage binding factor may be any substance, but especially a protein, which binds to DNA at a site of damage. It may be a DNA repair protein, for example a DNA repair enzyme such as photolyase or a protein encoded by one of the DNA repair genes in Table 1. Alternatively, the DNA damage binding factor may be a recognition protein such as an antibody which recognises DNA damage. One example of such a recognition protein is an antibody which binds specifically to cyclobutane pyrimidine dimers (CPDs) or more specifically to thymine dimers and are therefore able to be used for detecting a type of DNA damage induced by UV irradiation.

The above methodology enables a person of skill in the art to determine the location of any DNA damage within a sample of DNA, depending upon the number and nature of the DNA damage binding factors that are used in the method. Because the precise location of DNA damage in a genome can be detected, it is then possible, with knowledge of this location, to predict the functional significance of the DNA damage.

The tissue sample may be, for example a sample of cancerous tissue being targeted by a DNA damaging drug or normal tissue to be used for comparison with cancerous tissue or to be used in an assay for determining whether an agent causes DNA damage.

The DNA may be damaged DNA, for example in the case when the presence, location or amount of a DNA damaging drug is to be detected. Alternatively the DNA may be undamaged, for example when the method is used to determine whether or not an agent causes DNA damage. The term "DNA" is also intended to include DNA packaged as chromatin. In this case, the DNA-damage binding factor must be chosen so that it is able to penetrate the chromatin in order to bind to the damaged sites.

The shearing of step (3) above may be carried out using any appropriate shearing techniques such as the use of restriction enzymes or, more preferred, sonication which produces suitably smaller fragments of uniform size of DNA for the purpose of increasing the accuracy of the analysis.

In a preferred embodiment of the invention the DNA-damage binding factor is tagged with an immunoreactive binding molecule and part 4 above employs the use of an immunoreactive binding partner.

The DNA-damage binding factor may be labelled with at least one molecule that allows the protein, and so the DNA to which it is attached, or with which it is associated, to be determined when said DNA hybridises to the microarray. The label is typically a visual label, for example a chromophore, so that a coloured or light signal is produced when the DNA to which the DNA-damage binding factor is attached, or with which it is associated hybridises to the microarray.

When the optional amplification step (5) is employed, labelling may be achieved using primers that incorporate a chromophore label into the amplified material so that an enhanced amount of chromophore labelled DNA is produced. This amplified and labelled DNA is then hybridised to the microarray and the location of the DNA is visualised by observing the whereabouts of the label, for example a fluorescent signal, on the microarray.

In the method of the invention said DNA-damage binding factor is typically a DNA recognition protein, for example an antibody, that recognises DNA damage and/or a DNA repair enzyme such as, for example, photolyase or one or more of the enzymes encoded by the genes listed in Table 1 from a preferred species of organism having regard to optimisation of the invention.

When the DNA-damage binding protein is a DNA repair enzyme, it may be activated in order to repair any damage to the DNA prior to the optional amplification step (5). Therefore the process further includes the optional step of:
4b. allowing the DNA repair protein to repair any of the damaged DNA in the precipitate and/or the supernatant.

In many cases, it may also be useful to obtain information about the amount or extent of the DNA damage in a sample. Therefore, the method may further comprise comparing the amount of DNA fragments bound to or associated with the DNA repair protein with the amount of DNA fragments which are not so bound or associated.

This may be achieved by repeating step (5) of the method using the supernatant obtained when the DNA fragments are immunoprecipitated in step (4) above. The relative amounts of damaged (precipitate) and undamaged (supernatant) DNA can then be compared.

Alternatively, a sample of the sheared fragments obtained from step (3) can be amplified and labelled to give a measure of the total amount of DNA. This total amount can then be compared with the amount of DNA bound to the DNA repair protein.

To summarise, the method of the invention may after step (4) further comprise the steps of:
4a. taking the supernatant from the precipitation step (4) above;
4b. optionally allowing, the DNA repair protein to repair any of the damaged DNA in the precipitate and/or the supernatant;
5. amplifying and labelling the precipitated (damaged) fragments with a first label;

5a. either before, after or simultaneously with step (5) amplifying and labelling the (undamaged) DNA fragments in the supernatant with a second label which is distinguishable from the first label; and 6a. either before, after or simultaneously with step (6) exposing said amplified and labelled supernatant fragments from step (5a) to the microarray under conditions that enable the fragments to hybridise to the array;

7. detecting the locations and amounts of the first and second labels on the microarray and determining the location of any, or the, DNA damage and the relative amounts of the damaged and undamaged DNA.

As briefly outlined above, in addition to or instead of determining the amount of undamaged DNA in the sample, to determine the total amount of DNA in the sample.

Therefore the method may, in addition to or in place of the additional steps outlined above contain the steps of:

5b. amplifying and labelling a sample of the fragments obtained from step (3) with a third label; and 6b. either before, after or simultaneously with step (6) exposing said amplified and labelled supernatant fragments from step (5b) to the microarray under conditions that enable the fragments to hybridise to the array;

7. detecting the locations and amounts of the first, second (if present) and third labels on the microarray and determining the location of any, or the, DNA damage and the relative amounts of the damaged, undamaged and total DNA.

The method of the invention may be used for a number of purposes, for example in tracking the use of DNA damaging agents.

In some cases, the DNA damaging agent may be a DNA or chromatin binding drug. A number of agents used in the treatment of cancer are DNA binding and damaging agents, for example DNA cutters such as topoiomerase I poisons, for example topotecan, irinotecan and other camptothecin derivatives; topoiomerase II poisons for example etoposide, teniposide, daunomycin, adriamycin, idarubicin and mitoxantrone; bleomycin; DNA binders such as actinomycin D and mithramycin.

When the DNA damaging agent is a DNA binding drug, the method of the invention may be used to determine whether the drug has targeted the correct cells and/or the correct region of DNA within the target cells. Therefore the invention additionally comprises a method of determining whether a DNA damaging drug has bound to DNA of target cells, the method comprising carrying out a method as described above, wherein the tissue sample comprises target cells for the DNA binding drug and the presence of the DNA binding drug is indicated by the presence of DNA damage in the target cells. The method may also, of course, be used to determine the presence of drug in non-targeted cells.

Preferably, such a method also includes the step of determining whether the DNA damaging drug has bound to and damaged the desired target region of the genomic DNA and in this case, step (6) may further include determining whether the location of any DNA damage is the correct target location for the DNA damaging drug.

In addition, for this application, the quantitative methods described above may be used to determine the amount of DNA damaging drug in targeted cells compared with the amount in non-targeted cells. This is particularly useful for drugs which are specifically targeted to certain cell types, for example tumour cells or cells in certain organs where cancer or other diseases are to be treated. For this type of application, the quantitative method of the invention may be carried out twice with the tissue sample for each repetition comprising respectively targeted and non-targeted cells. The amount of DNA damaging drug in the cells will be directly related to the amount of DNA damage detected by the quantitative method of the invention.

A further application of the quantitative method is to determine the stability of the drug in the genome and/or its rate of metabolism. In this case, the quantitative method may be carried out at two or more separate times and the amounts of damaged DNA in the sample compared at those times in order to determine the rate of clearance of the drug from the DNA.

Our invention therefore enables us to monitor the use of DNA or chromatin binding drugs [eg DNA binding anticancer drugs] to determine whether they are targeting the correct DNA target sequences within the cells. It can also be used quantitatively to determine the extent of DNA damage and therefore the amount of DNA damaging drug in a sample. This enables us to monitor clearance of a drug from a tissue and develop a suitable drug treatment regime which can be individualised for each patient.

Therefore, there is also provided a method of determining a drug treatment regime for a patient, the method comprising carrying out a method as just described to determine the stability and/or rate of clearance of a DNA damaging drug in the genome and determining when the level in the DNA sample falls below a required level, at which time it is necessary to administer additional DNA damaging drug to a patient This method may also comprise the step of administering additional DNA damaging drug to the patient when the level in the DNA sample falls below the required level.

The method of the present invention may also be used as a screening method to identify compounds which cause DNA damage. In this case, the tissue sample will be chosen from normal cells and the DNA will be undamaged DNA. In this case, the method comprises the initial step of exposing some or all of the DNA to a compound to be tested. Although all of the DNA may be treated with the test compound, it is often advantageous to treat a portion of the DNA and to leave a portion untreated as a control. The DNA damage in the test and control samples can then be compared as a means of eliminating false positive results. When the quantitative methods described above are used it is possible to determine not only whether a test compound causes DNA damage but also the amount of damage which is caused.

The methodology also has application for testing compounds to determine whether they have the ability to repair DNA damage. In this case, the DNA repair protein used in the method of the invention will be a test DNA repair protein and the DNA in the sample will be damaged DNA. Advantageously, a quantitative method of the invention will be used. Such a method may comprise the steps of i. a first portion of the sample is treated by a quantitative method of the invention which includes step 4b, i.e. allowing the DNA repair protein to repair any of the damaged DNA in the precipitate and/or the supernatant and the extent of the DNA damage determined;

ii. a second portion of the sample is treated by a quantitative method of the invention which does not include step 4b and the extent of DNA damage determined; and iii. the extent of the damage in the two samples is compared to give a measure of the ability of the test DNA repair protein to repair damaged DNA.

Alternatively or additionally, the results can be compared with the results obtained when a reference DNA repair compound is used.

The invention also relates to a kit for carrying out the method and therefore in a further aspect of the invention there is provided a diagnostic kit for detecting DNA damage in a biological sample wherein the kit comprises at least one DNA damage-binding protein that is tagged with a binding partner;

a precipitating agent which is adapted to bind with said tagged protein; and a signalling agent or system which enables the DNA damage-binding protein to be visualised when any of the damaged DNA is hybridised to a microarray.

Other preferred features are as described above in relation to the method.

The kit may also provide a microarray to which the labelled DNA can be hybridised.

Our invention therefore enables us to screen for agents that damage DNA or agents that affect damaged DNA such as therapeutics; measure both the extent and the location of DNA damage; and measure the kinetics of DNA repair and or drug stability in the genome. These factors will enable us to identify within a given population, or even within a given individual, agents that are likely to affect the genome and so the health of a population, or individual; genes that are of particular importance for a given pathway and so, when damaged, lead to the breakdown of the pathway and the consequent diseases, for example, the invention could be used to identify a specific oncogene or to correlate a specific oncogene with a specific tumour type which in turn, has diagnostic implications for the population or individual concerned.

Our screening method also enables us to screen for potentially carcinogenic agents or indeed any pharmaceutical or chemical agents which need to be tested prior to their release and use. For example, we envisage that our invention may be suitably used when assaying for the potential of any new pharmaceutical product prior to its authorisation for use. Exposure of the human genome to the potential pharmaceutical and an assay for detecting any subsequent DNA damage would be a beneficial regulatory step because it would show whether the pharmaceutical in question had the ability to damage DNA and, if it did, the nature, extent and the reversibility of the DNA that was damaged.

We therefore believe that our invention is useful not only as a research tool but as a screening method for screening new and existing agents and a regulatory method for determining the safety of pharmaceuticals and chemicals prior to their subsequent use.

BRIEF DESCRIPTION OF THE DRAWINGS

An embodiment of the invention will now be described by way of example only with reference to the following Figures wherein.

DETAILED DESCRIPTION OF THE INVENTION

In the following example, the inventors have exemplified the method of the invention using an antibody which binds to CPDs. However, it should be stressed that the method would work equally well using any other DNA-damage binding factor. Examples of such proteins are well known and genes encoding these proteins are listed in Table 1. In addition, the inventors have also conducted experiments using photolyase from yeast as the DNA damage binding factor.

General Protocol

Figure 1:
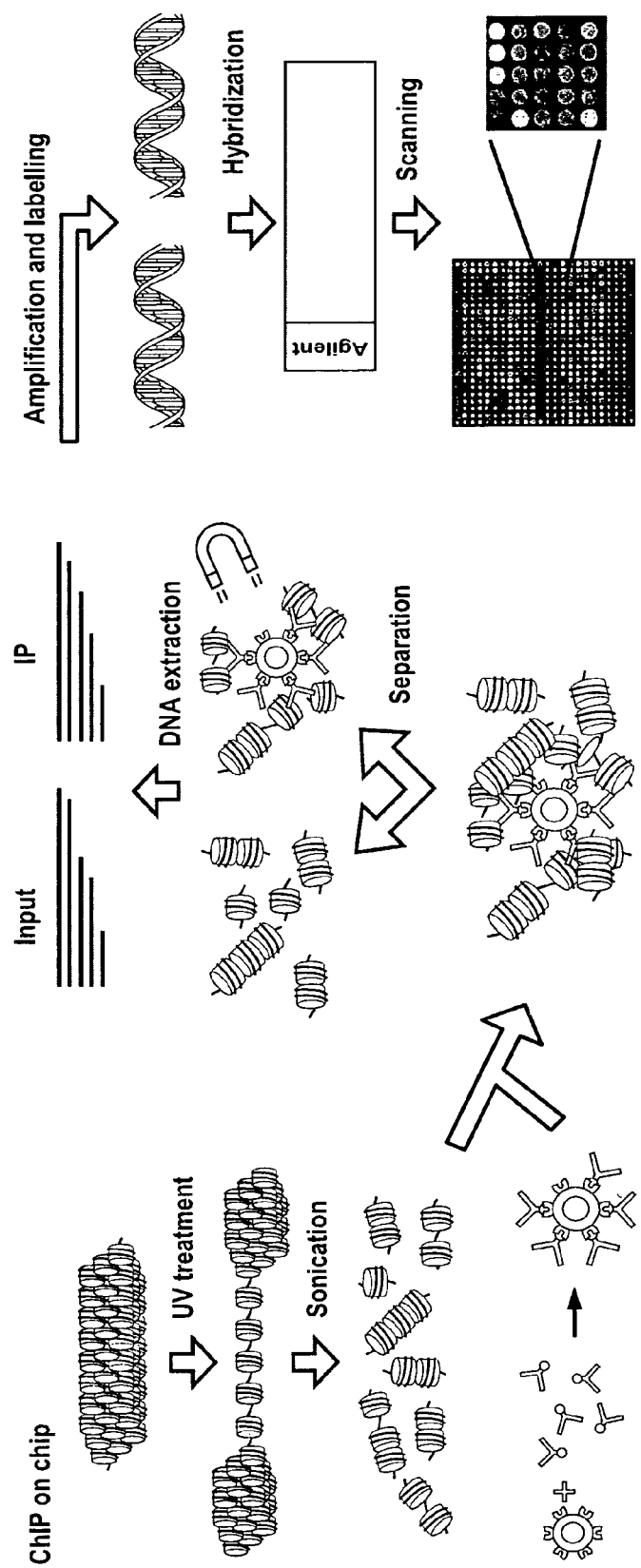
FIG. 1. illustrates the basic protocol for detection of pyrimidine dimers (CPDs) in DNA or chromatin. Cells are irradiated with UV to induce DNA damage (CPDs), following which, chromatin is isolated and sheared by sonication. UV-induced CPDs are detected in the DNA or chromatin using a tagged CPD specific antibody and then the labelled fragments containing CPDs are separated by immunoprecipitation (IP) from damage free DNA (supernatant). DNA is purified from IP and supernatant and amplified and labelled according to the Agilent protocol. The labelled IP samples can be hybridized to microarrays using a combination of supernatant or input samples. Finally the image is obtained by microarray scanner.

The basic protocol for detection of CPD in chromatin context is outlined in the FIG. 1. In addition to detecting CPDs on chromatin, this method also allows one to identify other repair proteins bond to chromatin with specific antibodies. The key stages are:

1 UV damage cells
2 Tagged protein binds DNA damage
3 Extract chromatin
4 Shear chromatin
5 Isolate damaged DNA from undamaged DNA using anti-Tag antibody.
6 DNA purification
7 Amplification
8 labelling From this point it is possible to continue the procedure in a number of ways. The diagram illustrates the various ways that the protocol can be developed. The standard Agilent procedure involves comparing signal from the immunoprecipitated material with the total Input material. Our preferred method is to compare the ratio of the immunoprecipitated chromatin with that which remains in the supernatant (see FIG. 1). This enables us to accurately measure the extent of DNA damage following exposure to UV radiation. This ratio will change as the removal of DNA damage occurs during DNA repair. It is also possible then to compare the material in the supernatant following immunoprecipitation with the true input (i.e sheared and tagged DNA before immunoprecipitation) as an additional control.

Basic protocol for direct detection of CPD in DNA is similar and can be summarised as follows: the key stages are:

1 UV damage cells
2 DNA extraction
3 Shear DNA by sonication
4 Separate damaged DNA (IP) from undamaged DNA (Supernatant) using anti-CPD antibody.
5 Amplification and labelling Example 1

Chromatin Immunoprecipitation (ChIP) on Chip Protocol and Visualisation of CPD Distribution, CPD Repair after 3 Hours of Treatment with Photolyase and Histone A3 Acetylation Changes DNA Damage Cells were exposed to UV radiation to induce DNA damage in a form including cyclobutane pyrimidine dimer (CPD) formation.

Preparation of Chromatin

Following the UV treatment, DNA was extracted either as naked DNA or as chromatin according to known methods. The extracted DNA or chromatin was then sheared by sonication. The protocol used for chromatin extraction and sonication is set out below.

1. Grow 100 ml cells to $2 \times 10^7$ cells/ml over night.
2. Add 3 ml of 37% formaldehyde to 100 ml culture. Shake for 10 min at r.t.
3. Stop cross-linking by adding 5.5 ml of 2.5M glycine. Shake for 5 min.
4. Collect cells, wash once with ice-cold PBS, and once with cold FA/SDS (+PMSF) buffer. Transfer
   the cells into 2 ml eppendorf during the wash.
5. Resuspend cells in 500 μl of FA/SDS (+PMSF) buffer.
6. Add 0.5 ml glass beads. Vortex with 2 ml turbomixer at 4° C. for 10 min.
7. Puncture a hole at the bottom of the eppendorf with red-hot needle, sit the 2 ml tube on the top
   of the 15 ml Corning tube. Spin at 2000 rpm for 2 min. Wash the beads 2×250 μl of FA/SDS
   (+PMSF) buffer.
8. Transfer the lysate into 2 ml eppendorf. Spin with a Beckman bench top centrifuge at 4° C. for
   20 min. Remove the supernatant by aspiration.
9. Resuspend the pellets with ~900 μl of FA/SDS (+PMSF) buffer. Transfer 1000 μl of the
   suspension into 15 ml Corning tube.
10. Sonicate the cell lysate with Biorupter: power "H", 30 s on 30 s off at 4° C. for 6 cycles.
11. Spin at maximum speed for 10 min on a bench top centrifuge. Transfer the supernatant into
    1.5 ml eppendorf and spin again at 4° C. for 20 min. Collect the supernatant (WCE). Flash freeze
    with liquid $N_2$.

Preparation of the Dynabeads (Mouse IgG)

The next step of the process was the detection of the CPDs induced in the DNA by the UV irradiation. This was achieved by reacting the fragments with a CPD-specific antibody. A number of CPD specific antibodies are known but the one used in this experiment was the anti-thymine dimer clone KTM53, available from Kamiya Biomedical Company, Seattle, Wash., USA. The process used for labelling the damaged DNA or chromatin fragments is set out below.

1. Take 50 μl of Dynabeads per sample.
2. 3 times washes with 500 μl PBS BSA 0.1% (4° C.)/sample. Mix with vortex and quick spin.
3. Resuspend the beads in 100 μl PBS BSA 0.1% per sample.
4. Add 2.5 μl of antibody (depend on individuals).
5. Incubate at 30° C. for 30 min at 1300 rpm in a Eppendorf Thermomixer.
6. Wash 3 times with 500 μl of PBS BSA 0.1% (4° C.)/sample.
7. Resuspend the beads in 50 μl of PBS BSA 0.1%. Separate into individual tubes depend on the sample numbers. Take the supernatant out.

Immunoprecipitation

The next step in the process is the immunoprecipitation of the labelled fragments containing the damaged DNA (CPDs) and the separation of damaged from undamaged DNA fragments. This was achieved by immunoprecipitation using the following protocol.

1. Defrost the chromatin sample on ice. Transfer 100 μl of the samples into the washed beads as IP sample, 20 μl into new tube for input.
2. Add 50 μl of 10×PBS BSA (10 mg/ml) into the samples, add PBS to 500 μl. Incubate for 2 h at 1300 rpm at 21° C. in a Eppendorf Thermomixer.
3. Wash with 500 μl of FA/SDS.
4. Wash 3 times with 1 ml of FA/SDS+NaCl (adjust the NaCl concentration to 500 mM).
5. The final wash is in an Eppendorf Thermomixer 10 min, 1300 rpm, 21° C.
6. Wash with 500 μl of Li solution.
7. Wash with 500 μl of cold TE. Pipetting out the solution.
8. Elute DNA with 125 μl of Pronase buffer at 65° C. at 900 rpm for 20 min.
9. Transfer the supernatant into a new tube. Add 6.25 μl of Pronase (20 mg/ml, $H_2O$). incubate at 37° C. for 1 h, then at 65° C. in water bath O.N.
10. To the Input (IN) samples (20 μl), add 80 μl of TE, 25 μl of 5× Pronase buffer, 6.25 μl of Pronase, then same as step 9.
11. Add 1 μl of 10 mg/ml of RNase to IP and IN samples. Incubate at 37° C. for 1 h.
12. Purifying the samples using Qiagen PCR purification kit. 50 μl (30+20) elution, collect all elute.
13. Take 5 μl samples for RT-PCR check.

Following the immunoprecipitation, both the damaged (precipitated) and the undamaged (supernatant) DNA were amplified using ligase-mediated PCR (LMPCR) according to the following method.

Blunt End 1. 40 μl of IP sample, 40 μl of IN sample (800× dilution with water). Keep the samples on ice.

|  | 1× | 5× |
|---|---|---|
| T4 DNA Pol Buffer | 11 μl | 55 μl |
| BSA (10 mg/ml) | 0.5 μl | 2.5 μl |
| dNTP (10 mM) | 1.0 μl | 5.0 μl |
| T4 DNA polymerase | 0.2 μl | 1.0 μl |
| $H_2O$ | 57.8 μl | 289 μl |
| Total | 70 μl | 350 μl |

Add 70 μl of the mix. Mix with pipetting, incubate at 12° C. (water bath) for 20 min.
2. Add 11.5 μl NaAc (3M pH5.2), 0.5 μl Glycogen (20 mg/ml). Mix with pipette.
3. Add 120 μl phenol/chloroform, vortex. Centrifuge 5 min at 15000 rpm at r.t.
4. Transfer the upper phase into a new tube.
5. Precipitate with 230 μl EtOH (−20° C.). Centrifuge at 15000 rpm for 15 min at 4° C.
6. Wash the pellet with 500 μl of cold 75% EtOH. Centrifuge for 5 min. Using pipette to remove the supernatant, avoiding the loss of the pellet.
7. Using Speed-Vac to dry the pellet for 7~min.

Ligation

Resuspend the pellets in 25 μl of $H_2O$. Add 25 μl Mix for ligation.

|  | 1× | 5× |
|---|---|---|
| $H_2O$ | 13 μl | 65 μl |
| DNA ligase buffer | 5 μl | 25 μl |
| linker hybride | 6.7 μl | 33.5 μl |
| T4 DNA ligase | 0.5 μl | 2.5 μl |
| Total | 25 μl | 125 μl |

Mix with pipetting, incubate at 16° C. (water bath) for O.N.

LM-PCR

1. Add 6 µl of NaAc (3M) to the ligation mixture.
2. precipitation with 130 µl EtOH (100%, ~20° C.).
3. Centrifugation 15 min, 15000 rpm, 4° C.
4. Wash with 500 µl EtOH (75%, cold). Spin for 5 min.
5. Dry by Speed-Vac for 7 min.
6. Resuspend the pellets in 25 ml of H$_2$O.
7. Add 15 µl PCR mix A

| Mix A (first PCR) | 1× | 5× |
| --- | --- | --- |
| 5× HFBuffer(Phusion) | 8 µl | 40 µl |
| dNTP (10 mM) | 1.25 µl | 6.25 µl |
| Oligo 102 (40 µM) | 1.25 µl | 6.25 µl |
| dd H$_2$O | 4.5 µl | 22.5 µl |
| Total | 15 µl | 75 µl |

| Mix B (first PCR) | 1× | 5× |
| --- | --- | --- |
| dd H$_2$O | 7 µl | 35 µl |
| 5× HFBuffer(Phusion) | 2 µl | 10 µl |
| Phusion Pol | 1 µl | 5 µl |
| Total | 10 µl | 50 µl |

PCR program PH-LM-15 (For Phusion DNA Pol, NEB)

| Step | Time | Temp |
| --- | --- | --- |
| 1 | 4 min | 55° C. |
| 2 | 3 min | 72° C. |
| 3 | 1 min | 98° C. |
| 4 | 10 s | 98° C. |
| 5 | 30 s | 55° C. |
| 6 | 1 min | 72° C. |
| 7 | go to 4, 14× | |
| 8 | 5 min | 72° C. |

8. Pause the Step 1 after 2 min running, add 10 µl of Polymerase Mix B, mix with pipetting, resume the cycles.
9. Add 475 µL ddH20 (total volume approximately 525 µL).
10. Put 5 µL of the resulting PCR product into a PCR tube (0.2 to 0.5 mL) for a second expansion.

| Mix for 2nd PCR | 1× | 5× |
| --- | --- | --- |
| 5× HFBuffer(Phusion) | 10 µl | 50 µl |
| dNTP (10 mM) | 1.25 µl | 6.25 µl |
| Oligo 102 (40 µM) | 1.25 µl | 6.25 µl |
| Phusion DNA Pol | 0.5 µl | 2.4 µl |
| dd H$_2$O | 32 µl | 160 µl |
| Total | 45 µl | 225 µl |

11. Put 45 µL of PCR mix to individual PCR tubes.
12. Run the PCR program PH-LM-25 below in a thermocycler:

| Step | Time | Temp |
| --- | --- | --- |
| 1 | 1 min | 98° C. |
| 2 | 10 s | 98° C. |
| 3 | 30 s | 55° C. |
| 4 | 1 min | 72° C. |
| 5 | go to 2, 24× | |
| 6 | 5 min | 72° C. |

13. Add 250 µL precipitation mix to each tube.

| Precipitation Mix | 1× | 5× |
| --- | --- | --- |
| Ammonium Acetate (7.5M) | 25 µl | 125 µl |
| Ethanol | 225 µl | 1125 µl |
| Total | 250 µl | 1250 µl |

14. Cool for 30 minutes at −80° C.
15. Spin at 20,000×g for 10 minutes at 4° C. to pellet DNA.
16. Wash the pellets with 500 µL of 70% EtOH.
17. Dry the pellets for 10 minutes with a vacuum dessicator, and resuspend each pellet in 50 µL H2O.
18. Measure DNA concentration with NanoDrop (NanoDrop Technologies) (use 10-fold dilutions, if necessary) and normalize all samples to 100 ng/µL.

Labelling

Next, the damaged and undamaged DNA samples were differentially labelled (in the dark) using the Invitrogen BioPrime® Total Genomic Labeling System according to the following protocol.

1. Genomic DNA samples should be prepared in TE or in water with EDTA in a volume of 22 µl.
   DNA sample in water 17.6 µl
   5 mM EDTA 4.4 µl
   Total 22 µl
2. Add Alexa Fluor 3 2× Reaction Mix 25 µl; or
   Alexa Fluor 5 2× Reaction Mix 25 µl into 22 µl DNA samples (total 47 µl).
3. Gently pipette up and down to mix and incubate at 95° C. in dark for 5 min. Immediately cool on ice for 5 min.
4. On ice, add 3 µl of Exo-Klenow Fragment to each tube (total 50 µl).
5. Vortex tubes briefly and centrifuge to collect the contents.
6. Incubate at 37° C. for 2 hours in a heat block in dark.
7. After the incubation, if you are storing the reaction for any length of time prior to purification, add 5 µl of 0.5M EDTA to each tube to quench the reaction. Or you can proceed directly to purification step using a invitrogen column.
8. Purification with invitrogen column following the instruction. Elute the DNA in 55 µl Blution Buffer E1.
9. Take 5 µl of the sample for O.D. check at 260, 280, 320, 555, 650, 750 nm.
10. Combine the cy5 and cy3 pair together to 100 µl volume.
11. To the 100 µl of sample, add 12 µl of NaAc (3M), 5 µl of Polyacrylamide (2.5 µg/ml). Add 2.5 volume of EtOH (~290 µl), mix, 10 min at 80° C.
12. Centrifugation 15000 rpm for 15 min. Take the supernatant out by pipetting. The pellets are fragile (blue), be careful.
13. Wash with 300 µl EtOH (75%, cold). Spin for 5 min at 15000 rpm.
14. Pipetting out the supernatant, 5 min Speed-Vac drying. Store at −20° C.

Hybridization to Agilent® Chip

Finally, the labelled samples were hybridized to an Agilent® chip Containing yeast genome wide arrays. This was achieved using the following method.

1. prepare the hybridization mix;

| Stock | Final concent. | Vol. for 1× | |
|---|---|---|---|
| Na-MES pH 6.9 (500 mM) | 50 mM | 50 µl | |
| NaCl (5M) | 500 mM | 50 µl | |
| EDTA (0.5M) | 6 mM | 6 µl | |
| Sarcosine (20%) | 0.5% | 12.5 µl | |
| Formamide | 30% | 150 µl | |
| Herring Sperm DNA (250 µg/µl) | 250 ng | 1 µl | (BD) |
| Yeast tRNA (4.3 µg/µl) | 80 µg | 18.6 µl | Invitrogen (Gibco) |
| H₂O | | 207.9 µl | |

2. Resuspend the pellets with 4 µl H2O. Add 496 µl of the Mix.
3. Heat at 95° C. for 3 min.
4. incubate at 40° C. for 15 min in the oven.
5. Centrifuge briefly.
6. Mount the hybridization chamber.
7. Pipetting out 500 µl sample on the cover slide. Carefully lay the chip down to touch the liquid and make sure no bubbles form (Agilent side face down).
8. Close the chamber. Incubate in the oven for 17±2 hours at 40° C.

Wash the Chip
Array washing buffer I
 SSPE 20×300 ml
 Sarcosine 20% 250 µl
 H₂O to 1 L (700 ml)
Array washing buffer II
 SSPE 20×3 ml
 H₂O to 1 L (997 ml)

1. Take the hybridization chamber out the oven, transfer the slides to a container filled with washing buffer I. Separate the slides inside the washing solution with a pair of tweezers.
2. Rinse the chip slide in the washing solution I for seconds and transfer carefully to a slide rack.
3. Soak the rack in a washing buffer I container. Covered in foil, leave it on shaking platform for 5 min with gently shaking (60 rpm).
4. Transfer the rack from buffer I to a container with buffer II. Covered in foil, leave it on shaking platform for 5 min with gently shaking (60 rpm).
5. Take the rack out from the buffer II very slowly, keep no drop of liquid on the surface of the slide. Use tissue paper to dry the edge of the slide.

Similar experiments have also been conducted using photolyase derived from yeast as the DNA damage binding factor. In these experiments, the bound photolyase was activated in one sample of the immunoprecipitated damaged DNA and the repair process allowed to proceed for three hours. The remainder of the procedure was then carried out as described above for both the unrepaired sample and the repaired sample as well as the undamaged (supernatant) DNA.

Figure 2:
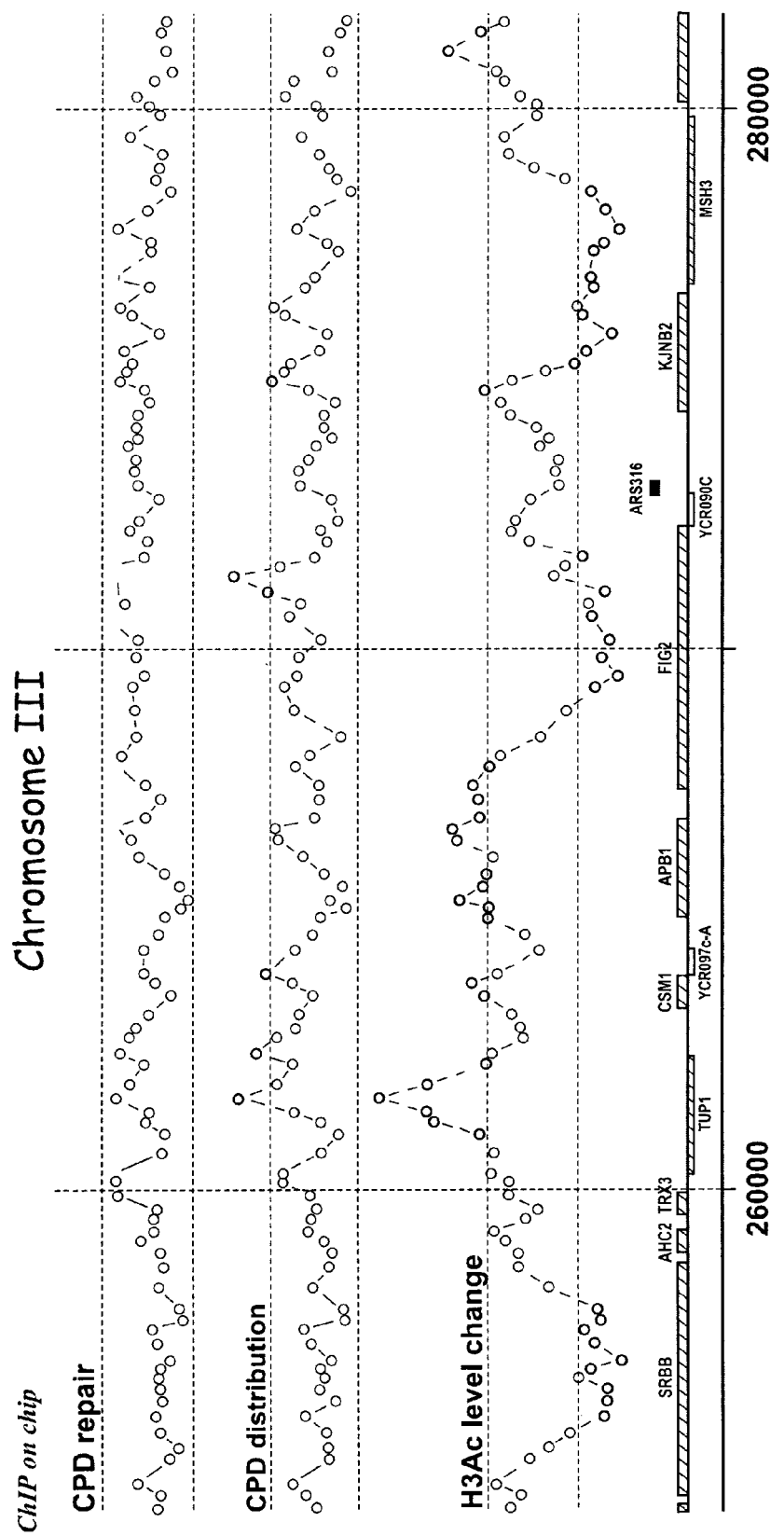
FIG. 2: is part of an image generated from the data provided by a microarray scanner, following scanning of a Chip on Chip experimental array. It shows data for the distribution of UV induced CPDs in yeast in a small section of the yeast genome (line entitled "CPD distribution"); data showing the changes in CPD levels in yeast DNA following three hours of repair after UV exposure in the same small section of the genome (line entitled "CPD repair"); and data showing the changes in histone H3 acetylation in response to UV for the same small section of the yeast genome (line entitled "H3Ac level change").

We have generated genome wide data for the distribution of UV induced CPDs in yeast and this is shown for a small section of the yeast genome in FIG. 2 (line entitled "CPD distribution"). Present technology theoretically allows the location of CPDs to be detected to an accuracy of 5 base pairs. We have also measured the changes in CPD levels in yeast DNA following three hours of repair after UV exposure. Again, we have generated genome-wide data and a exemplary data for a small section of the genome is again shown in FIG. 2 ("CPD repair"). Comparing the CPD levels at 0 and 3 hours after UV allows an accurate genome-wide view of CPD repair during the period. We also measured the changes in histone H3 acetylation in response to UV. Once again, genome wide data was obtained and FIG. 2 illustrates the relevant data for a small section of the yeast genome (H3Ac level change). Changes in chromatin or chromatin-associated proteins often, occur in response to DNA damage and during DNA damage repair.

The data obtained for yeast demonstrates the principle of the invention but it would also be possible to obtain equivalent data for other species including humans. For example, using the newly available one million feature whole genome human arrays, it would be possible to obtain similar results for the human genome. Because of the increased size of the human genome as compared with the yeast genome, present technology allows the detection of CPDs to within around 100 base pairs in the human genome.

The invention claimed is:

1. A method for locating DNA damage in a tissue sample comprising:
   1) obtaining a sample of DNA from the tissue sample;
   2) exposing said DNA to at least one selected DNA-damage binding factor which binds to DNA at a site of damage whereby a precise location of the damage can be located, which damage binding factor is selected from one of a DNA repair enzyme or an antibody which recognizes DNA damage and is tagged with or comprises a given binding molecule;
   3) shearing the DNA to produce fragments thereof;
   4) precipitating fragments that include, or are associated with the tagged DNA-damage binding factor by binding the said tag to a selected binding partner in order to isolate fragments of DNA that include, or are associated with, said DNA-damage binding factor;
   5) optionally amplifying said precipitated fragments and then labeling said precipitated fragments; and
   6) exposing said labeled precipitated fragments to a genome-wide microarray under conditions that enable the fragments to hybridize to the array whereby the location of any, or the, DNA damage can be determined having regard to the location of the hybridization fragments with respect to the array;
   wherein step 2) may be carried out either before or after step 3).

2. A method as claimed in claim 1, wherein the tissue sample is a sample of cancerous tissue being targeted by a DNA damaging drug.

3. A method as claimed in claim 1 wherein the tissue sample is a sample of normal tissue.

4. A method as claimed in claim 1, wherein the DNA is damaged DNA.

5. A method as claimed in claim 1, wherein the DNA is normal DNA.

6. A method as claimed in claim 1, wherein the shearing step 3) is carried out using restriction enzymes or sonication.

7. A method as claimed in claim 1, wherein the DNA-damage binding factor is tagged with an immunoreactive binding molecule and step 4) employs the use of an immunoreactive binding partner.

8. A method as claimed in claim 7 wherein the DNA-damage binding factor is labeled with at least one molecule that allows the binding factor, and so the DNA to which it is attached, or with which it is associated, to be determined when said DNA hybridises to the microarray.

9. A method as claimed in claim 8, wherein the label is a visual label.

10. A method as claimed in claim 1, which includes the optional amplification step 5) and wherein labeling is achieved using primers that incorporate a chromophore label into the amplified material so that an enhanced amount of chromophore labeled DNA is produced.

11. A method as claimed in claim 1 wherein the DNA-damage binding factor is a DNA repair protein and the process further includes the optional step of:
   4b allowing the DNA repair protein to repair any of the damaged DNA in the precipitate and/or the supernatant.

12. A method as claimed in claim 1, further comprising the steps of:
   4a) taking the supernatant from the precipitation step 4) above;
   4b) where the DNA-damage binding factor is a DNA repair protein, optionally allowing the DNA repair protein to repair any of the damaged DNA in the precipitate and/or the supernatant;
   5) amplifying and labeling the precipitated damaged fragments with a first label;
   5a) either before, after or simultaneously with step 5) amplifying and labeling the undamaged DNA fragments in the supernatant with a second label which is distinguishable from the first label; and
   6a) either before, after or simultaneously with step 6) exposing said amplified and labeled supernatant fragments from step 5a) to the microarray under conditions that enable the fragments to hybridize to the array; and
   7) detecting the locations and amounts of the first and second labels on the microarray and determining the location of any, or the, DNA damage and the relative amounts of the damaged and undamaged DNA.

13. A method as claimed in claim 1, further including the steps of:
   5b) amplifying and labeling a sample of the fragments obtained from step 3) with a third label; and
   6b) either before, after or simultaneously with step 6) exposing said amplified and labeled supernatant fragments from step 5b) to the microarray under conditions that enable the fragments to hybridize to the array;
   7) detecting the presence, locations and amounts of the first, second and third labels on the microarray and determining the location of any, or the, DNA damage and the relative amounts of the damaged, undamaged and total DNA.

14. A method of determining whether a DNA damaging drug has bound to DNA of target cells, the method comprising:
   exposing a tissue sample to a DNA damaging drug; and carrying out the method as claimed in claim 1;
   wherein the tissue sample comprises target cells for the DNA damaging drug and the presence of the DNA damaging drug is indicated by the presence of DNA damage in the target cells.

15. A method of determining whether a DNA damaging drug has bound to DNA of non-target cells, the method comprising carrying out a method as claimed in claim 1, wherein the tissue sample comprises non-target cells for the DNA damaging drug and the presence of the DNA damaging drug is indicated by the presence of DNA damage in the non-target cells.

16. A method of determining whether a DNA damaging drug has bound to and damaged a desired target region of the genomic DNA, the method comprising carrying out a method as claimed in claim 1, wherein step 6) further includes determining whether the location of any DNA damage is the correct target location for the DNA damaging drug.

17. A method of determining the amount of DNA damaging drug in targeted cells compared with the amount in non-targeted cells, the method comprising carrying out a method as claimed in claim 12, for a first tissue sample comprising target cells for a DNA damaging drug and a second tissue sample comprising non-target cells for the DNA damaging drug and comparing the amounts of DNA damage in the two samples as measured in step 7).

18. A method of determining the stability of a DNA damaging drug in the genome and/or its rate of clearance from the genome, the method comprising carrying out a method as claimed in claim 12 for a DNA sample at two or more separate times and comparing the amounts of damaged DNA in the sample at the two or more separate times in order to determine the stability and/or rate of clearance of the drug from the DNA sample.

19. A method of determining a drug treatment regime for a patient, the method comprising carrying out a method as claimed in claim 18 and determining the time at which the level of DNA damaging drug in the DNA sample falls below a required level, at which time it is necessary to administer additional DNA damaging drug to a patient.

20. A method as claimed in claim 19, further comprising the step of administering additional DNA damaging drug to the patient when the level in the DNA sample falls below the required level.

21. A method as claimed in claim 14, wherein the DNA damaging drug is selected from the group consisting of DNA cutters, DNA binders, topoiomerase I poisons, topotecan, irinotecan, camptothecin and camptothecin derivatives, topoiomerase II poisons, etoposide, teniposide, daunomycin, adriamycin, idarubicin, mitoxantrone, bleomycin, actinomycin D and mithramycin.

22. A screening method to identify compounds which cause DNA damage, the method comprising carrying out a method as claimed in claim 1, wherein the tissue sample is chosen from normal cells and the DNA is undamaged DNA, wherein the method further comprises the initial step of exposing some or all of the DNA to a compound to be tested.

23. A method as claimed in claim 22, further including the step of providing a control sample which has not been treated with the test compound and comparing the DNA damage in the two samples.

24. A method as claimed in claim 22 wherein the screening method is a quantitative method.

25. A method of determining whether a test compound has the ability to repair DNA damage, the method comprising conducting a method as claimed in claim 1 in which the test compound is used as the DNA repair protein and the DNA in the sample is damaged DNA.

26. A method as claimed in claim 25, wherein:
   i) a first portion of the sample is treated by a method of claim 12 or claim 13 which includes step 4b, i.e. allowing the DNA repair protein to repair any of the damaged DNA in the precipitate and/or the supernatant and the extent of the DNA damage determined;
   ii) a second portion of the sample is treated by a method of claim 13 or claim 14 which does not include step 4b and the extent of DNA damage determined; and
   iii) the extent of the damage in the two samples is compared to give a measure of the ability of the test DNA repair protein to repair damaged DNA.

27. A method as claimed in claim 25 wherein the results are compared with the results obtained when a reference DNA repair compound is used.

28. A kit for carrying out a method as claimed in claim 1, the kit comprising:
   at least one DNA-damage binding factor that is tagged with a binding partner;
   a precipitating agent which is adapted to bind with said tagged protein; and
   a signaling agent or system which enables the DNA-damage binding factor to be visualised when any of the damaged DNA is hybridised to a microarray.

29. A kit as claimed in claim 28 further comprising a microarray to which the labelled DNA can be hybridised.

30. A method of determining whether a DNA damaging drug has bound to DNA of target cells, the method comprising carrying out a method as claimed in claim 12, wherein the tissue sample comprises target cells for the DNA damaging drug and the presence of the DNA damaging drug is indicated by the presence of DNA damage in the target cells.

31. A method of determining whether a DNA damaging drug has bound to DNA of target cells, the method comprising carrying out a method as claimed in claim 13, wherein the tissue sample comprises target cells for the DNA damaging drug and the presence of the DNA damaging drug is indicated by the presence of DNA damage in the target cells.

32. A method of determining whether a DNA damaging drug has bound to DNA of non-target cells, the method comprising carrying out a method as claimed in claim 12, wherein the tissue sample comprises non-target cells for the DNA damaging drug and the presence of the DNA damaging drug is indicated by the presence of DNA damage in the non-target cells.

33. A method of determining whether a DNA damaging drug has bound to DNA of non-target cells, the method comprising carrying out a method as claimed in claim 13, wherein the tissue sample comprises non-target cells for the DNA damaging drug and the presence of the DNA damaging drug is indicated by the presence of DNA damage in the non-target cells.

34. A method of determining whether a DNA damaging drug has bound to and damaged a desired target region of the genomic DNA, the method comprising carrying out a method as claimed in claim 12, wherein step 6) further includes determining whether the location of any DNA damage is the correct target location for the DNA damaging drug.

35. A method of determining whether a DNA damaging drug has bound to and damaged a desired target region of the genomic DNA, the method comprising carrying out a method as claimed in claim 13, wherein step 6) further includes determining whether the location of any DNA damage is the correct target location for the DNA damaging drug.

36. A method of determining the amount of DNA damaging drug in targeted cells compared with the amount in non-targeted cells, the method comprising carrying out a method as claimed in claim 13, for a first tissue sample comprising target cells for a DNA damaging drug and a second tissue sample comprising non-target cells for the DNA damaging drug and comparing the amounts of DNA damage in the two samples as measured in step 7).

37. A method of determining the stability of a DNA damaging drug in the genome and/or its rate of clearance from the genome, the method comprising carrying out a method as claimed in claim 13 for a DNA sample at two or more separate times and comparing the amounts of damaged DNA in the sample at the two or more separate times in order to determine the stability and/or rate of clearance of the drug from the DNA sample.

38. A screening method to identify compounds which cause DNA damage, the method comprising carrying out a method as claimed in claim 12, wherein the tissue sample is chosen from normal cells and the DNA is undamaged DNA, wherein the method further comprises the initial step of exposing some or all of the DNA to a compound to be tested.

39. A screening method to identify compounds which cause DNA damage, the method comprising carrying out a method as claimed in claim 13, wherein the tissue sample is chosen from normal cells and the DNA is undamaged DNA, wherein the method further comprises the initial step of exposing some or all of the DNA to a compound to be tested.

40. A method of determining whether a test compound has the ability to repair DNA damage, the method comprising conducting a method as claimed in claim 12 in which the test compound is used as the DNA repair protein and the DNA in the sample is damaged DNA.

41. A method of determining whether a test compound has the ability to repair DNA damage, the method comprising conducting a method as claimed in claim 13 in which the test compound is used as the DNA repair protein and the DNA in the sample is damaged DNA.

42. A method as claimed in claim 40, wherein:
   i) a first portion of the sample is treated by a method including step 4b, i.e. allowing the DNA repair protein to repair any of the damaged DNA in the precipitate and/or the supernatant and the extent of the DNA damage determined;
   ii) a second portion of the sample is treated by a method which does not include step 4b and the extent of DNA damage determined; and
   iii) the extent of the damage in the two samples is compared to give a measure of the ability of the test DNA repair protein to repair damaged DNA.

43. A method as claimed in claim 41, wherein:
   i) a first portion of the sample is treated by a method including step 4b, i.e. allowing the DNA repair protein to repair any of the damaged DNA in the precipitate and/or the supernatant and the extent of the DNA damage determined;
   ii) a second portion of the sample is treated by a method which does not include step 4b and the extent of DNA damage determined; and
   iii) the extent of the damage in the two samples is compared to give a measure of the ability of the test DNA repair protein to repair damaged DNA.

44. A method as claimed in claim 42 wherein the results are compared with the results obtained when a reference DNA repair compound is used.

45. A method as claimed in claim 43 wherein the results are compared with the results obtained when a reference DNA repair compound is used.

46. A method as claimed in claim 15, wherein the DNA damaging drug is selected from the group consisting of DNA cutters, DNA binders, topoiomerase I poisons, topotecan, irinotecan, camptothecin and camptothecin derivatives, topoiomerase II poisons, etoposide, teniposide, daunomycin, adriamycin, idarubicin, mitoxantrone, bleomycin, actinomycin D and mithramycin.

47. A method as claimed in claim 16, wherein the DNA damaging drug is selected from the group consisting of DNA cutters, DNA binders, topoiomerase I poisons, topotecan, irinotecan, camptothecin and camptothecin derivatives, topoiomerase II poisons, etoposide, teniposide, daunomycin, adriamycin, idarubicin, mitoxantrone, bleomycin, actinomycin D and mithramycin.

48. A method as claimed in claim 17, wherein the DNA damaging drug is selected from the group consisting of DNA cutters, DNA binders, topoiomerase I poisons, topotecan, irinotecan, camptothecin and camptothecin derivatives, topoiomerase II poisons, etoposide, teniposide, daunomycin, adriamycin, idarubicin, mitoxantrone, bleomycin, actinomycin D and mithramycin.

49. A method as claimed in claim 18, wherein the DNA damaging drug is selected from the group consisting of DNA cutters, DNA binders, topoiomerase I poisons, for example topotecan, irinotecan, camptothecin and camptothecin derivatives, topoiomerase II poisons, etoposide, teniposide, daunomycin, adriamycin, idarubicin, mitoxantrone, bleomycin, actinomycin D and mithramycin.

50. A method as claimed in claim 19, wherein the DNA damaging drug is selected from the group consisting of DNA cutters, DNA binders, topoiomerase I poisons, topotecan, irinotecan, camptothecin and camptothecin derivatives, topoiomerase II poisons, etoposide, teniposide, daunomycin, adriamycin, idarubicin, mitoxantrone, bleomycin, actinomycin D and mithramycin.

51. A method as claimed in claim 20, wherein the DNA damaging drug is selected from the group consisting of DNA cutters, DNA binders, topoiomerase I poisons, topotecan, irinotecan, camptothecin and camptothecin derivatives, topoiomerase II poisons, etoposide, teniposide, daunomycin, adriamycin, idarubicin, mitoxantrone, bleomycin, actinomycin D and mithramycin.

52. A method of determining a drug treatment regime for a patient, the method comprising carrying out a method as claimed in claim 37 and determining the time at which the level of DNA damaging drug in the DNA sample falls below a required level, at which time it is necessary to administer additional DNA damaging drug to a patient.

53. A method as claimed in claim 52, further comprising the step of administering additional DNA damaging drug to the patient when the level in the DNA sample falls below the required level.

54. A method as claimed in claim 1, wherein step 5) comprises amplifying and labeling the precipitated fragments.

* * * * *